(12) United States Patent
Rieck et al.

(10) Patent No.: US 7,119,049 B2
(45) Date of Patent: Oct. 10, 2006

(54) OXATHIINECARBOXAMIDES

(75) Inventors: Heiko Rieck, Foy les Lyon (FR); Ralf Dunkel, Monheim (DE); Hans-Ludwig Elbe, Wuppertal (DE); Ulrike Wachendorff-Neumann, Neuwied (DE); Astrid Mauler-Machnik, Leichlingen (DE); Karl-Heinz Kuck, Langenfeld (DE)

(73) Assignee: Bayer Cropscience AG, Leverkusen (DE)

( * ) Notice: Subject to any disclaimer, the term of this patent is extended or adjusted under 35 U.S.C. 154(b) by 29 days.

(21) Appl. No.: 10/515,044

(22) PCT Filed: May 15, 2003

(86) PCT No.: PCT/EP03/05103

§ 371 (c)(1),
(2), (4) Date: May 12, 2005

(87) PCT Pub. No.: WO03/099804

PCT Pub. Date: Dec. 4, 2003

(65) Prior Publication Data

US 2005/0203171 A1   Sep. 15, 2005

(30) Foreign Application Priority Data

May 23, 2002   (DE)   ................. 102 22 886

(51) Int. Cl.
*A01N 43/54*   (2006.01)
*C07D 327/06*   (2006.01)
*A61K 31/385*   (2006.01)

(52) U.S. Cl. .............. 504/240; 504/242; 549/14; 549/362; 549/441; 514/433

(58) Field of Classification Search ................. 549/362, 549/441; 504/240, 242
See application file for complete search history.

(56) References Cited

U.S. PATENT DOCUMENTS

| | | | | |
|---|---|---|---|---|
| 3,249,499 A | * | 5/1966 | Von Schmeling et al. .. | 514/433 |
| 3,393,202 A | * | 7/1968 | Kulka et al. ............... | 549/14 |
| 3,399,214 A | * | 8/1968 | Kulka et al. ............... | 549/14 |
| 3,538,225 A | | 11/1970 | Dudarevitch et al. ....... | 424/276 |
| 3,657,449 A | * | 4/1972 | Davis et al. ................ | 514/433 |
| 5,416,103 A | | 5/1995 | Eicken et al. .............. | 514/355 |
| 5,438,070 A | | 8/1995 | Eicken et al. .............. | 514/403 |
| 5,633,218 A | | 5/1997 | Spedding et al. ........... | 504/228 |
| 2004/0082572 A1 | | 4/2004 | Pineiro et al. .............. | 514/220 |

FOREIGN PATENT DOCUMENTS

| | | |
|---|---|---|
| CA | 2106497 | 3/1994 |
| EP | 545 099 | 6/1993 |
| FR | 1 477 061 | 4/1967 |
| JP | 8-176112 | 7/1996 |
| JP | 2001-302605 | 10/2001 |
| WO | 02/08197 | 1/2002 |

OTHER PUBLICATIONS

Synth. Commun., 30, (month unavailable) 2000, pp. 665-669, Pravin M. Bendale et al, "Silica Gel Supported Chromium Trioxide: An Efficient Reagent for Oxidative Cleavage of Oximes to Carbonyl Compounds Under Mild Condition"

Synth. Commun., 29, (month unavailable) 1999, pp. 1697-1701, A.R. Hajipour et al., "Solid-Phase Synthesis of Oximes"

* cited by examiner

*Primary Examiner*—Sabiha Qazi
(74) *Attorney, Agent, or Firm*—Richard E. L. Henderson

(57) ABSTRACT

This invention relates to novel oxathiinecarboxamides of the formula (I)

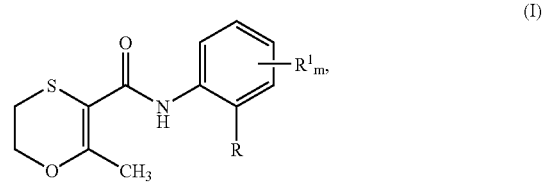

in which R, $R^1$ and m are as defined in the disclosure, to a plurality of processes for preparing these substances and to their use for controlling unwanted micro-organisms.

13 Claims, No Drawings

OXATHIINECARBOXAMIDES

The present patent application has been filed under 35 U.S.C. 371 as a national stage application of PCT/EP03/05103, filed May 15, 2003, which was published in German as International Patent Publication WO 03/099804 on Dec. 4, 2003, which is entitled to the right of priority of German Patent Application 102 22 886.8, filed May 23, 2002.

The present invention relates to novel oxathiinecarboxamides, to a plurality of processes for their preparation and to their use for controlling unwanted micro-organisms.

It is already known that numerous carboxanilides have fungicidal properties (compare, for example, EP-A 0 545 099, EP-A 0 591 699, DE-A 16 17 921, JP-A 2001-302605 and JP-A 8-176112). Thus, the oxathiinecarboxamides N-(4'-fluoro-1,1'-biphenyl-2-yl)-2-methyl-5,6-dihydro-1,4-oxathiine-3-carboxamide, N-(3'-fluoro-1,1'-biphenyl-2-yl)-2-methyl-5,6-dihydro-1,4-oxathiine-3-carboxamide, N-(2'-fluoro-1,1'-biphenyl-2-yl)-2-methyl-5,6-dihydro-1,4-oxathiine-3-carboxamide, N-(3'-chloro-1,1'-biphenyl-2-yl)-2-methyl-5,6-dihydro-1,4-oxathiine-3-carboxamide and N-(3'-methyl-1,1'-biphenyl-2-yl)-2-methyl-5,6-dihydro-1,4-oxathiine-3-carboxamide are already known from EP-A 0 545 099. The activity of these substances is good; however, in some cases, for example at low application rates, it is unsatisfactory.

This invention now provides novel oxathiinecarboxamides of the formula (I)

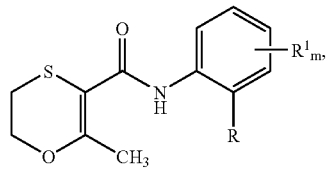

(I)

in which $R^1$ represents fluorine, m represents 0, 1 or 2,

R represents one of the groupings below,

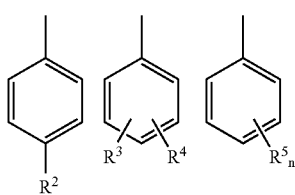

$R^2$ represents chlorine, bromine, iodine, cyano, nitro, $C_1$–$C_8$-alkyl, $C_1$–$C_8$-alkoxy, $C_1$–$C_8$-alkylthio, $C_1$–$C_6$-haloalkyl, $C_1$–$C_6$-haloalkoxy or $C_1$–$C_6$-haloalkylthio having in each case from 1 to 13 fluorine, chlorine and/or bromine atoms, $R^3$ and $R^4$ independently of one another represent fluorine, chlorine, bromine, iodine, cyano, nitro, $C_1$–$C_8$-alkyl, $C_1$–$C_8$-alkoxy, $C_1$–$C_8$-alkylthio, $C_1$–$C_6$-haloalkyl, $C_1$–$C_6$-haloalkoxy or $C_1$–$C_6$-haloalkylthio having in each case 1 to 13 fluorine, chlorine and/or bromine atoms, n represents 3, 4 or 5 and $R^5$ represents identical or different radicals from the group consisting of fluorine, chlorine, bromine, iodine, cyano, nitro, $C_1$–$C_8$-alkyl, $C_1$–$C_8$-alkoxy, $C_1$–$C_8$-alkylthio, $C_1$–$C_6$-haloalkyl, $C_1$–$C_6$-haloalkoxy or $C_1$–$C_6$-haloalkylthio having in each case 1 to 13 fluorine, chlorine and/or bromine atoms.

Furthermore, it has been found that oxathiinecarboxamides of the formula (I) are obtained when a) carboxylic acid derivatives of the formula (II)

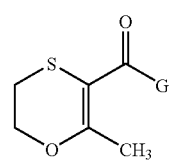

(II)

in which

G halogen, hydroxyl or $C_1$–$C_6$-alkoxy, are reacted with aniline derivatives of the formula (III)

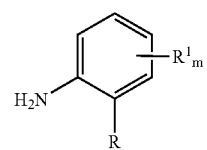

(III)

in which

R, $R^1$ and m are as defined above, if appropriate in the presence of a catalyst, if appropriate in the presence of an acid binder and if appropriate in the presence of a diluent, or b) carboxamide derivatives of the formula (IV)

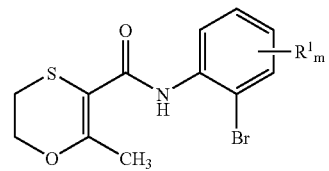

(IV)

in which $R^1$ and m are as defined above, are reacted with boronic acid derivatives of the formula (V)

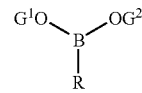

(V)

in which

R is as defined above and

G$^1$ and G$^2$ each represent hydrogen or together represent tetramethylethylene, in the presence of a catalyst, if appropriate in the presence of an acid binder and if appropriate in the presence of a diluent, or c) carboxamide boronic acid derivatives of the formula (VI)

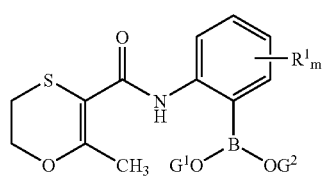

(VI)

in which

R$^1$ and m are as defined above and

G$^1$ and G$^2$ each represent hydrogen or together represent tetramethylethylene, are reacted with phenyl derivatives of the formula (VII)

(VII)

in which

R is as defined above in the presence of a catalyst, if appropriate in the presence of a an acid binder and if appropriate in the presence of a diluent, or d) carboxamide derivatives of the formula (IV)

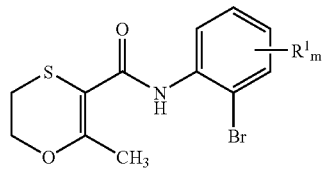

(IV)

in which

R$^1$ and m are as defined above, are reacted with phenyl derivatives of the formula (VII)

(VII)

in which

R is as defined above, in the presence of a palladium or platinum catalyst and in the presence of 4,4,4',4',5,5,5',5'-octamethyl-2,2'-bis-1,3,2-dioxaborolane, if appropriate in the presence of an acid binder and if appropriate in the presence of a diluent.

Finally, it has been found that the novel oxathiinecarboxamides of the formula (I) have very good microbicidal properties and can be used for controlling unwanted microorganisms both in crop protection and in the protection of materials.

Surprisingly, the oxathiinecarboxamides of the formula (I) according to the invention have considerably better fungicidal activity than the constitutionally most similar active compounds of the prior art having the same direction of action.

The formula (I) provides a general definition of the oxathiinecarboxamides of the invention.

Preference is given to oxathiinecarboxamides of the formula (I), in which

R$^1$ represents fluorine, m represents 0, 1 or 2,

R represents one of the groupings below,

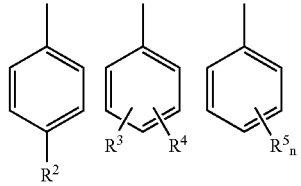

R$^2$ represents chlorine, bromine, C$_1$–C$_6$-alkyl, C$_1$–C$_6$-alkoxy, C$_1$–C$_6$-alkylthio, C$_1$–C$_4$-haloalkyl, C$_1$–C$_4$-haloalkoxy, C$_1$–C$_4$-haloalkylthio having in each case 1 to 9 fluorine, chlorine and/or bromine atoms, R$^2$ furthermore represents cyano, R$^3$ and R$^4$ independently of one another represent fluorine, chlorine, bromine, C$_1$–C$_6$-alkyl, C$_1$–C$_6$-alkoxy, C$_1$–C$_6$-alkylthio, C$_1$–C$_4$-haloalkyl, C$_1$–C$_4$-haloalkoxy, C$_1$–C$_4$-haloalkylthio having in each case 1 to 9 fluorine, chlorine and/or bromine atoms, n represents 3, 4 or 5 and R$^5$ represents identical or different radicals from the group consisting of fluorine, chlorine, bromine, C$_1$–C$_6$-alkyl, C$_1$–C$_6$-alkoxy, C$_1$–C$_6$-alkylthio, C$_1$–C$_4$-haloalkyl, C$_1$–C$_4$-haloalkoxy, C$_1$–C$_4$-haloalkylthio having in each case 1 to 9 fluorine, chlorine and/or bromine atoms.

Particular preference is given to oxathiinecarboxamides of the formula (I) in which R$^1$ represents fluorine, m represents 0 or 1, R represents one of the groupings below,

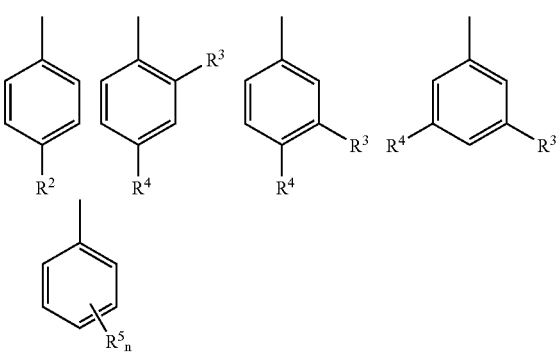

R$^2$ represents chlorine, bromine, methyl, ethyl, n-propyl, i-propyl, n-butyl, i-butyl, s-butyl, t-butyl, methoxy, ethoxy, methylthio, ethylthio, trichloromethyl, trifluoromethyl, difluoromethyl, difluorochloromethyl, difluoromethoxy, trifluoromethoxy, trifluoromethylthio, difluorochloromethyl-thio, R² furthermore represents cyano, R³ and R⁴ independently of one another represent fluorine, chlorine, bromine, methyl, ethyl, n-propyl, i-propyl, n-butyl, i-butyl, s-butyl, t-butyl, methoxy, ethoxy, methylthio, ethylthio, trichloromethyl, trifluoromethyl, difluoromethyl, difluorochloromethyl, difluoromethoxy, trifluoromethoxy, trifluoromethylthio, difluorochloromethylthio, n represents 3 or 4 and R⁵ represents identical or different radicals from the group consisting of fluorine, chlorine, bromine, methyl, ethyl, n-propyl, i-propyl, n-butyl, i-butyl, s-butyl, t-butyl, methoxy, ethoxy, methylthio, ethylthio, trichloromethyl, trifluoromethyl, difluoromethyl, difluorochloromethyl, difluoromethoxy, trifluoromethoxy, trifluoromethylthio, difluorochloromethylthio Very particular preference is given to oxathiinecarboxamides of the formula (I), in which R¹ represents fluorine, m represents 0 or 1, R represents one of the groupings below,

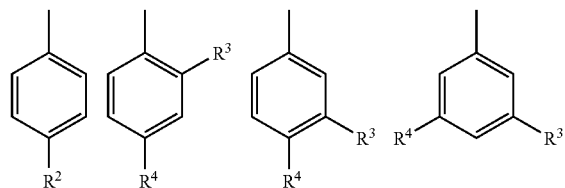

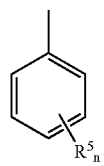

R² represents chlorine, bromine, methyl, ethyl, n-propyl, i-propyl, n-butyl, i-butyl, s-butyl, t-butyl, methoxy, ethoxy, methylthio, ethylthio, trichloromethyl, trifluoromethyl, difluoromethyl, trifluoromethoxy, trifluoromethylthio, R² furthermore represents cyano, R³ and R⁴ independently of one another represent fluorine, chlorine, bromine, methyl, ethyl, n-propyl, i-propyl, n-butyl, i-butyl, s-butyl, t-butyl, methoxy, ethoxy, methylthio, ethylthio, trichloromethyl, trifluoromethyl, difluoromethyl, trifluoromethoxy, trifluoromethylthio, n represents 3 and R⁵ represents identical or different radicals from the group consisting of fluorine, chlorine, bromine, methyl, ethyl, n-propyl, i-propyl, n-butyl, i-butyl, s-butyl, t-butyl, methoxy, ethoxy, methylthio, ethylthio, trichloromethyl, trifluoromethyl, difluoromethyl, trifluoromethoxy, trifluoromethylthio.

Especially preferred are oxathiinecarboxamides of the formula (I), in which

R¹ represents fluorine, m represents 0 or 1,

R represents one of the groupings below,

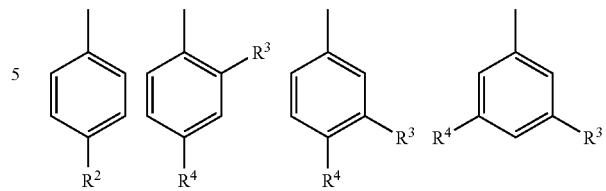

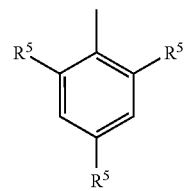

R² represents chlorine, bromine, t-butyl, methoxy, methylthio, trichloromethyl, trifluoromethyl, trifluoromethoxy, trifluoromethylthio, R² furthermore represents cyano, R³ and R⁴ independently of one another represent fluorine, chlorine, methyl, methoxy, methylthio, trifluoromethyl, trifluoromethoxy, trifluoromethylthio, R⁵ represents identical or different radicals from the group consisting of fluorine, chlorine, methyl, methoxy, methylthio, trifluoromethyl, trifluoromethoxy, trifluoromethylthio Emphasis is furthermore given to compounds of the formula (I) in which m represents 0.

Emphasis is furthermore given to compounds of the formula (I) in which R represents the grouping

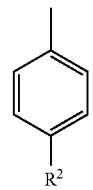

and R² as the general, preferred, particularly preferred, very particularly preferred and/or especially preferred meanings given above.

Emphasis is furthermore given to compounds of the formula (I) in which R represents one of the groupings below

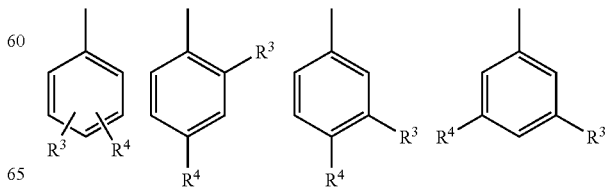

and $R^3$ and $R^4$ have the general, preferred, particularly preferred, very particularly preferred and/or especially preferred meanings given above.

Emphasis is furthermore given to compounds of the formula (I) in which $R^3$ and $R^4$ independently of one another represent fluorine, chlorine or bromine.

Emphasis is furthermore given to compounds of the formula (I-a)

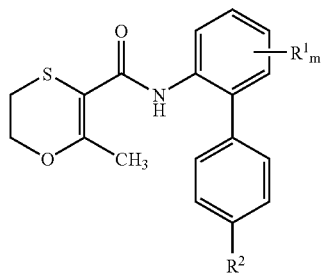

(I-a)

in which
$R^1$ represents fluorine,
m represents 0 or 1,
$R^2$ represents chlorine, bromine, methyl, ethyl, n-propyl, i-propyl, n-butyl, i-butyl, s-butyl, t-butyl, methoxy, ethoxy, methylthio, ethylthio, trichloromethyl, trifluoromethyl, difluoromethyl, difluorochloromethyl, difluoromethoxy, trifluoromethoxy, trifluoromethylthio, difluorochloromethylthio,
$R^2$ furthermore represents cyano.

Emphasis is furthermore given to compounds of the formula (I-b)

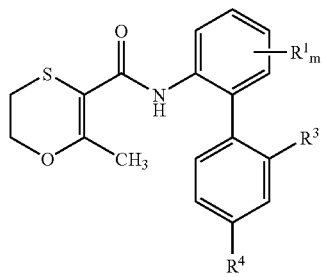

(I-b)

in which
$R^1$ represents fluorine,
m represents 0 or 1,
$R^3$ and $R^4$ independently of one another represent fluorine, chlorine, bromine, methyl, ethyl, n-propyl, i-propyl, n-butyl, i-butyl, s-butyl, t-butyl, methoxy, ethoxy, methylthio, ethylthio, trichloromethyl, trifluoromethyl, difluoromethyl, difluorochloromethyl, difluoromethoxy, trifluoromethoxy, trifluoromethylthio, difluorochloromethylthio.

Emphasis is furthermore given to compounds of the formula (I-c)

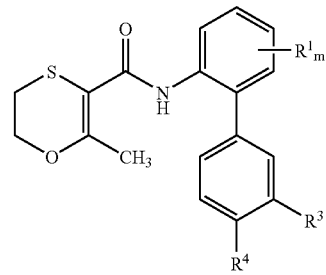

(I-c)

in which
$R^1$ represents fluorine,
m represents 0 or 1,
$R^3$ and $R^4$ independently of one another represent fluorine, chlorine, bromine, methyl, ethyl, n-propyl, i-propyl, n-butyl, i-butyl, s-butyl, t-butyl, methoxy, ethoxy, methylthio, ethylthio, trichloromethyl, trifluoromethyl, difluoromethyl, difluorochloromethyl, difluoromethoxy, trifluoromethoxy, trifluoromethylthio, difluorochloromethylthio.

Emphasis is furthermore given to compounds of the formula (I-d)

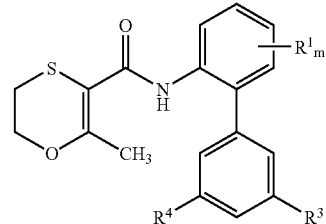

(I-d)

in which
$R^1$ represents fluorine,
m represents 0 or 1,
$R^3$ and $R^4$ independently of one another represent fluorine, chlorine, bromine, methyl, ethyl, n-propyl, i-propyl, n-butyl, i-butyl, s-butyl, t-butyl, methoxy, ethoxy, methylthio, ethylthio, trichloromethyl, trifluoromethyl, difluoromethyl, difluorochloromethyl, difluoromethoxy, trifluoromethoxy, trifluoromethylthio, difluorochloromethylthio.

Saturated or unsaturated hydrocarbon radicals, such as alkyl or alkenyl, can in each case be straight-chain or branched as far as this is possible, including in combination with heteroatoms, such as, for example, in alkoxy.

Optionally substituted radicals can be mono- or polysubstituted, where in the case of polysubstitution the substituents can be identical or different.

Halogen-substituted radicals, such as, for example, haloalkyl, are mono- or polyhalogenated. In the case of polyhalogenation, the halogen atoms can be identical or different. Here, halogen represents fluorine, chlorine, bromine and iodine, in particular fluorine, chlorine and bromine.

However, the general or preferred radical definitions or illustrations given above can also be combined with one another as desired, i.e. including combinations between the respective ranges and preferred ranges. The definitions apply both to the end products and to the precursors and intermediates. Moreover, individual definitions may not apply.

Using 2-methyl-5,6-dihydro-1,4-oxathiine-3-carbonyl-chloride and 4'-chloro-2'-fluoro-1,1'-biphenyl-2-amine as starting materials, the course of the process (a) according to the invention can be illustrated by the formula scheme below.

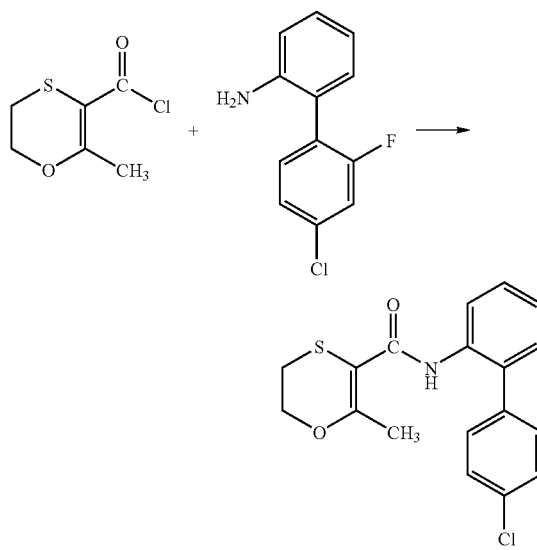

Using N-(2-bromophenyl)-2-methyl-5,6-dihydro-1,4-oxathiine-3-carboxamide and 4-chloro-2-fluorophenylboronic acid as starting materials and a catalyst, the course of the process (b) according to the invention can be illustrated by the formula scheme below.

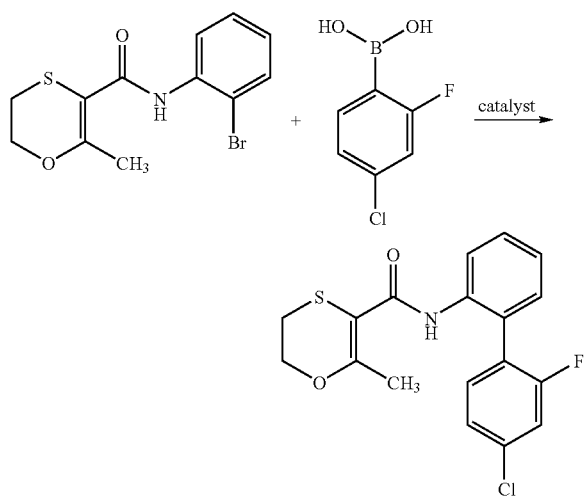

Using 2-{[(2-methyl-5,6-dihydro-1,4-oxathiin-3-yl)carbonyl]amino}phenylboronic acid and 1-bromo-4-chloro-2-fluorobenzene as starting materials and a catalyst, the course of the process (c) according to the invention can be illustrated by the formula scheme below.

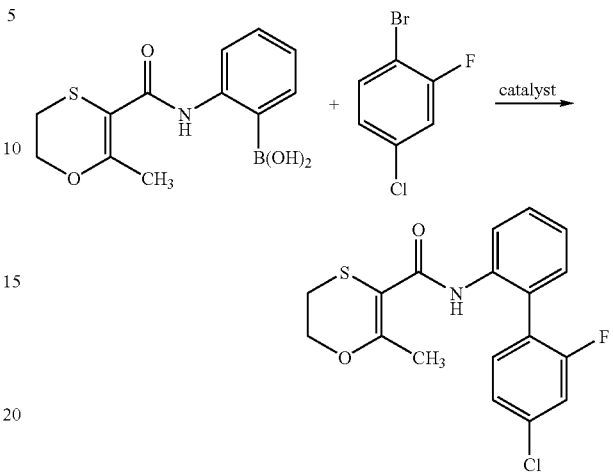

Using N-(2-bromophenyl)-2-methyl-5,6-dihydro-1,4-oxathiine-3-carboxamide and 1-bromo-4-chloro-2-fluorobenzene as starting materials and a catalyst and 4,4,4',4',5,5,5',5'-octamethyl-2,2'-bis-1,3,2-dioxaborolane, the course of the process (d) according to the invention can be illustrated by the formula scheme below.

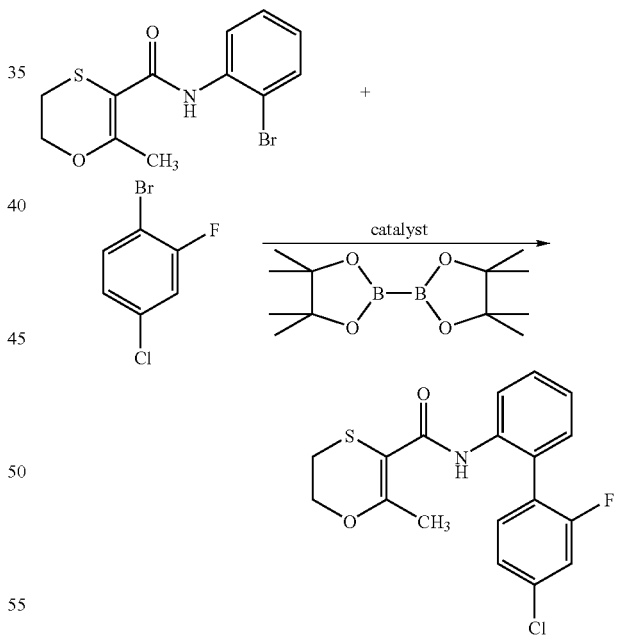

Explanation of the Processes and Intermediates

The formula (II) provides a general definition of the carboxylic acid derivatives required as starting materials for carrying out the process (a) according to the invention. In this formula, G preferably represents chlorine, bromine, hydroxyl, methoxy or ethoxy, particularly preferably chlorine, hydroxyl or methoxy, very particularly preferably chlorine.

The carboxylic acid derivative of the formula (II) are known or can be prepared by known processes (cf. EP-A 0 545 099 and EP-A 0 589 313).

The formula (III) provides a general definition of the analine derivatives required as reaction components for carrying out the process (a) according to the invention. In this formula, R, $R^1$ and m preferably have those meanings which have already been mentioned in connection with the description of the compounds of the formula (I) according to the invention as being preferred, particularly preferred, very particularly preferred or especially preferred for these radicals or these indices.

The aniline derivatives of the formula (III) are known and/or some of them can be prepared by known methods (cf. EP-A 0 545 099 and EP-A 0 589 301). Aniline derivatives of the formula (III) are obtained, for example, by e) reacting 2-haloaniline derivatives of the general formula (VIII)

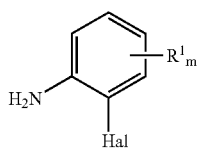
(VIII)

in which
$R^1$ and m are as defined above and
Hal represents halogen,
with boronic acid derivatives of the formula (V)

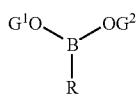
(V)

in which
R is as defined above, and
if appropriate in the presence of an acid binder, if appropriate in the presence of an inert organic diluent and if appropriate in the presence of a catalyst, or f) reacting anilineboronic acids of the formula (IX)

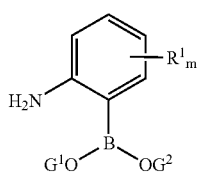
(IX)

in which
$R^1$, m, $G^1$ and $G^2$ are as defined above
with phenyl derivatives of the formula (VII)

(VII)

in which
R is as defined above,
if appropriate in the presence of an acid binder, if appropriate in the presence of an inert organic diluent and if appropriate in the presence of a catalyst.

The formula (VIII) provides a general definition of the two-haloaniline derivatives required as reaction components for carrying out the process (e) according to the invention. In this formula, $R^1$ and m preferably have those meanings which have already been mentioned in connection with the description of the compounds of the formula (I) according to the invention as being preferred, particularly preferred, very particularly preferred or especially preferred for these radicals or indices. Hal preferably represents fluorine, chlorine or bromine, particularly preferably chlorine or bromine.

The 2-haloaniline derivatives of the formula (VIII) are known and/or can be prepared from the corresponding nitro compounds by reduction.

The boronic acid derivatives of the formula (V) furthermore required as starting materials for carrying out the process (e) according to the invention are explained in more detail below, in connection with the process (b) according to the invention.

Formula (IX) provides a general definition of the anilineboronic acids required as reaction components for carrying out the process (f) according to the invention. In this formula, $R^1$ and m preferably have those meanings which have already been mentioned in connection with the description of the compounds of the formula (I) according to the invention as being preferred, particularly preferred, very particularly preferred or especially preferred for these radicals or these indices. $G^1$ and $G^2$ preferably each represent hydrogen or together represent tetramethylethylene.

The anilineboronic acids of the formula (IX) are known and/or can be obtained by known methods.

The phenyl derivatives of the formula (VII) furthermore required as starting materials for carrying out the process (f) according to the invention are explained in more detail below, in connection with the process (d) according to the invention.

The formula (IV) provides a general definition of the carboxamide derivatives required as starting materials for carrying out the processes (b) and (d) according to the invention. In this formula, $R^1$ and m preferably have those meanings which have already been mentioned in connection with the description of the compounds of the formula (I) according to the invention as being preferred, particularly preferred, very particularly preferred or especially preferred for these radicals or these indices.

The carboxamide derivatives of the formula (IV) are known or can be prepared by known processes (for example from a carboxylic acid derivative of the formula (III) and a 2-bromoaniline derivative).

The formula (V) provides a general definition of the boronic acid derivatives required as starting materials for carrying out the processes (b) and (e) according to the invention. In this formula, R preferably has those meanings which have already been mentioned in connection with the description of the compounds of the formula (I) according to the invention as being preferred, particularly preferred, very particularly preferred and especially preferred for this radical. $G^1$ and $G^2$ preferably each represent hydrogen or together represent tetramethylethylene.

The boronic acid derivatives of the formula (V) are known and/or can be prepared by known processes (cf., for example, WO 01/90084 and U.S. Pat. No. 5,633,218).

They are obtained, for example, by g) reacting phenyl derivatives of the formula (VII)

(VII)

in which
R is as defined above,
with boric acid esters of the formula (X)

(X)

in which
$R^6$ represents $C_1$–$C_4$-alkyl,
in the presence of magnesium, if appropriate in the presence of a diluent (for example tetrahydrofuran).

The formula (X) provides a general definition of the boric acid esters required as reaction components for carrying out the process (g) according to the invention. In this formula, $R^6$ preferably represents methyl, ethyl, n- or i-propyl, particularly preferably methyl or ethyl.

The boric acid esters of the formula (X) are known chemicals for synthesis.

The formula (VI) provides a general definition of the carboximide boronic acid derivatives required as reaction components for carrying out the process (c) according to the invention. In this formula, $R^1$ and m preferably have those meanings which have already been mentioned in connection with the description of the compounds of the formula (I) according to the invention as being preferred, particularly preferred, very particularly preferred or especially preferred for these radicals or these indices. $G^1$ and $G^2$ preferably each represent hydrogen or together represent tetramethylethylene.

The carboxamide boronic acid derivatives of the formula (VI) are known and/or can be prepared by known processes.

The formula (VII) provides a general definition of the phenyl derivatives required as starting materials for carrying out the processes (c), (d), (f) and (g) according to the invention. In this formula, R preferably has those meanings which have already been mentioned in connection with the description of the compounds of the formula (I) according to the invention as being preferred, particularly preferred, very particularly preferred or especially preferred for this radical.

The phenyl derivatives of the formula (VII) are known or can be prepared by known processes (cf. Synth. Commun. 2000, 30, 665–669, Synth. Commun. 1999, 29, 1697–1701).

Suitable acid binders for carrying out the processes (a), (b), (c), (d), (e) and (f) according to the invention are in each case all inorganic and organic bases customary for such reactions. Preference is given to using alkaline earth metal or alkali metal hydroxides, such as sodium hydroxide, calcium hydroxide, potassium hydroxide, or else ammonium hydroxide, alkali metal carbonates, such as sodium carbonate, potassium carbonate or potassium bicarbonate, sodium bicarbonate, alkali metal or alkaline earth metal acetates, such as sodium acetate, potassium acetate, calcium acetate, and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU). However, it is also possible to work without the addition of an acid binder, or to employ an excess of the amine component so that it simultaneously acts as acid binder.

Suitable diluents for carrying out the processes (a), (b), (c), (d), (e) and (f) according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decaline; chlorobenzene, dichlorobenzene, dichloromethane, chloroform, carbon tetrachloride, dichloroethane or trichloroethane; ethers, such as diethyl ether, diisopropyl ether, methyl-t-butyl ether, methyl-t-amyl ether, dioxane, tetrahydrofuran, 1,2-dimethoxyethane, 1,2-diethoxyethane or anisol; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide, esters, such as methyl acetate or ethyl acetate; sulfoxides, such as dimethyl sulfoxide, or sulfones, such as sulfolane.

When carrying out the processes (a), (b), (c), (d), (e) and (f) according to the invention, the reaction temperatures can in each case be varied within a relatively wide range. In general, the processes are carried out at temperatures between 0° C. and 140° C., preferably between 10° C. and 120° C.

The processes (a), (b), (c), (d), (e) and (f) according to the invention are generally each carried out under atmospheric pressure. However, in each case it is also possible to operate under elevated or reduced pressure.

When carrying out the process (a) according to the invention, in general 1 mol or else an excess of aniline derivative of the formula (III) and from 1 to 3 mol of acid binder are employed per mole of carboxylic acid derivative of the formula (II). However, it is also possible to employ the reaction components in other ratios. Work-up is carried out by customary methods. In general, water is added to the reaction mixture and the organic phase is separated off and, after drying, concentrated under reduced pressure. The residue that remains may, if appropriate, be freed of any impurities that may still be present using customary methods, such as chromatography or recrystallization.

When carrying out the process (b) according to the invention, in general 1 mol or else an excess of boronic acid derivative of the formula (V) and from 1 to 5 mol of acid binder are employed per mole of carboxamide derivative of the formula (IV). However, it is also possible to employ the reaction components in other ratios. Work-up is carried out by customary methods. In general, water is added to the reaction mixture and the precipitate is separated off and dried. The reside that remains may, if appropriate, be freed of any impurities that may still be present using customary methods, such as chromatography or recrystallization.

When carrying out the process (c) according to the invention, in general 1 mol or else an excess of phenyl derivative of the formula (VII) and from 1 to 10 mol of acid binder and from 0.5 to 5 mol % of a catalyst are employed per mole of carboxamide boronic acid derivative of the formula (VI). However, it is also possible to employ the reaction components in other ratios. Work-up is carried out by customary methods. In general, water is added to the reaction mixture and the precipitate is separated off and dried. The residue that remains may, if appropriate, be freed of any impurities that may still be present using customary methods, such as chromatography or recrystallization.

When carrying out the process (d) according to the invention, in general 1 mol or else an excess of phenyl derivative of the formula (VII) and from 1 to 5 mol of acid binder and from 1 to 5 mol of a catalyst are employed per mole of carboxamide derivative of the formula (IV). However, it is also possible to employ the reaction components in other ratios. Work-up is carried out by customary methods. In general, water is added to the reaction mixture and the precipitate is separated off and dried. The residue that remains may, if appropriate, be freed of any impurities that may still be present using customary methods, such as chromatography or recrystallization.

The substances according to the invention have potent microbicidal activity and can be employed for controlling unwanted micro-organisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

*Xanthomonas* species, such as, for example, *Xanthomonas campestris* pv. *oryzae;*
*Pseudomonas* species, such as, for example, *Pseudomonas syringae* pv. *lachrymans;*
*Erwinia* species, such as, for example, *Erwinia amylovora;*
*Pythium* species, such as, for example, *Pythium ultimum;*
*Phytophthora* species, such as, for example, *Phytophthora infestans;*
*Pseudoperonospora* species, such as, for example, *Pseudoperonospora humuli* or *Pseudoperonospora cubensis;*
*Plasmopara* species, such as, for example, *Plasmopara viticola;*
*Bremia* species, such as, for example, *Bremia lactucae;*
*Peronospora* species, such as, for example, *Peronospora pisi* or *P. brassicae;*
*Erysiphe* species, such as, for example, *Erysiphe graminis;*
*Sphaerotheca* species, such as, for example, *Sphaerotheca graminis;*
*Podosphaera* species, such as, for example, *Podosphaera leucotricha;*
*Venturia* species, such as, for example, *Venturia inaequalis;*
*Pyrenophora* species, such as, for example, *Pyrenophora teres* or *P. graminea* (conidia form: *Drechslera*, syn: *Helminthosporium*);
*Cochliobolus* species, such as, for example, *Cochliobolus sativus* (conidia form: *Drechslera*, syn: *Helminthosporium*);
*Uromyces* species, such as, for example, *Uromyces appendiculatus;*
*Puccinia* species, such as, for example, *Puccinia recondita;*
*Sclerotinia* species, such as, for example, *Sclerotinia sclerotiorum;*
*Tilletia* species, such as, for example, *Tilletia caries;*
*Ustilago* species, such as, for example, *Ustilago nuda* or *Ustilago avenae;*
*Pellicularia* species, such as, for example, *Pellicularia sasakii;*
*Pyricularia* species, such as, for example, *Pyricularia oryzae;*
*Fusarium* species, such as, for example, *Fusarium culmorum;*
*Botrytis* species, such as, for example, *Botrytis cinerea;*
*Septoria* species, such as, for example, *Septoria nodorum;*
*Leptosphaeria* species, such as, for example, *Leptosphaeria nodorum;*
*Cercospora* species, such as, for example, *Cercospora canescens;*
*Alternaria* species, such as, for example, *Alternaria brassicae;* and
*Pseudocercosporella* species, such as, for example, *Pseudocercosporella herpotrichoides.*

The active compounds according to the invention also have very good fortifying action in plants. Accordingly, they can be used for mobilizing the defences of the plant against attack by unwanted micro-organisms.

In the present context, plant-fortifying (resistance-inducing) substances are to be understood as meaning those substances which are capable of stimulating the defence system of plants such that, when the treated plants are subsequently inoculated with unwanted micro-organisms, they show substantial resistance against these micro-organisms.

In the present case, unwanted micro-organisms are to be understood as meaning phytopathogenic fungi, bacteria and viruses. Accordingly, the substances according to the invention can be used to protect plants for a certain period after the treatment against attack by the pathogens mentioned. The period for which protection is provided generally extends over 1 to 10 days, preferably 1 to 7 days, after the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention are also suitable for increasing the yield of crops. In addition, they show reduced toxicity and are well tolerated by plants.

At certain concentrations and application rates, the active compounds according to the invention can also be used as herbicides, for influencing plant growth and for controlling animal pests. They can also be used as intermediates and precursors for the synthesis of further active compounds.

The active compounds according to the invention can be used to treat all plants and parts of plants. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment of the plants and the parts of plants with the active compounds according to the invention is carried out directly or by action on their surroundings, habitat or storage space, according to customary treatment methods, for example by dipping, spraying, evaporating, atomizing, broadcasting, spreading-on and, in the case of propagation material, in particular in the case of seeds, furthermore by one- or multi-layer coating.

In the protection of materials, the compounds according to the invention can be employed for protecting industrial materials against infection with, and destruction by, undesired micro-organisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, micro-organisms. Parts of production plants, for example cooling-water circuits, which may be impaired by the proliferation of micro-organisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Micro-organisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes), and against slime organisms and algae.

Micro-organisms of the following genera may be mentioned as examples:
*Alternaria*, such as *Alternaria tenuis*,
*Aspergillus*, such as *Aspergillus niger*,
*Chaetomium*, such as *Chaetomium globosum*,
*Coniophora*, such as *Coniophora puetana*,
*Lentinus*, such as *Lentinus tigrinus*,
*Penicillium*, such as *Penicillium glaucum*,
*Polyporus*, such as *Polyporus versicolor*,
*Aureobasidium*, such as *Aureobasidium pullulans*,
*Sclerophoma*, such as *Sclerophoma pityophila*,
*Trichoderma*, such as *Trichoderma viride*,
*Escherichia*, such as *Escherichia coli*,
*Pseudomonas*, such as *Pseudomonas aeruginosa*, and
*Staphylococcus*, such as *Staphylococcus aureus*.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide.

Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention can be used as such or in their formulations, also in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Examples of suitable mixing components are the following:

Fungicides:
aldimorph, ampropylfos, ampropylfos potassium, andoprim, anilazine, azaconazole, azoxystrobin,
benalaxyl, benodanil, benomyl, benzamacril, benzamacril-isobutyl, bialaphos, binapacryl, biphenyl, bitertanol, blasticidin-S, bromuconazole, bupirimate, buthiobate,
calcium polysulphide, carpropamide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
edifenphos, epoxiconazole, etaconazole, ethirimol, etridiazole,
famoxadon, fenapanil, fenarimol, fenbuconazole, fenfuram, fenhexamide, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulphamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, iprovalicarb, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulphocarb, methfuroxam, metiram, metomeclam, metsulphovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, picoxystrobin, pimaricin, piperalin, polyoxin, polyoxorim, probenazole, prochloraz, procymidone, propamocarb, propanosine-sodium, propiconazole, propineb, pyraclostrobin, pyrazophos, pyrifenox, pyrimethanil, pyroquilon, pyroxyfur, quinconazole, quintozene (PCNB), quinoxyfen, sulphur and sulphur preparations, spiroxamines, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, trifloxystrobin, triflumizole, triforine, triticonazole, uniconazole, validamycin A, vinclozolin, viniconazole, zarilamide, zineb, ziram and also Dagger G, OK-8705, OK-8801, α-(1,1-dimethylethyl)-β-(2-phenoxyethyl)-1H-1,2,4-triazole-1-ethanol, α-(2,4-dichlorophenyl)-β-fluoro-β-propyl-1H-1,2,4-triazole-1-ethanol, α-(2,4-dichlorophenyl)-β-methoxy-α-methyl-1H-1,2,4-triazole-1-ethanol, α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, 1-(2,4-dichlorophenyl)-2-(1H-1,2,4-triazol-1-yl)-ethanone O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoromethyl-1,3-thiazole-5-carboxanilide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrole-2,5-dione, 3,5-dichloro-N-[cyano[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)-oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholine-hydrochloride, ethyl [(4-chlorophenyl)-azo]-cyanoacetate, potassium hydrogen carbonate, methanetetrathiol sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetamide, N-(2-chloro-4-nitrophenyl)-4-methyl-3-nitro-benzenesulphonamide, N-(4-cyclohexylphenyl)-1,4,5,6-tetrahydro-2-pyrimidineamine, N-(4-hexylphenyl)-1,4,5,6-tetrahydro-2-pyrimidineamine, N-(5-chloro-2-methylphenyl)-2-methoxy-N-(2-oxo-3-oxazolidinyl)-acetamide, N-(6-methoxy-3-pyridinyl)-cyclopropanecarboxamide, N-[2,2,2-trichloro-1-[(chloroacetyl)-amino]-ethyl]-benzamide, N-[3-chloro-4,5-bis-(2-propinyloxy)-phenyl]-N'-methoxy-methanimidamide, N-formyl-N-hydroxy-DL-alanine-sodium salt, O,O-diethyl[2-(dipropylamino)-2-oxoethyl]-ethylphosphoramidothioate, O-methyl S-phenyl phenylpropylphosphoramidothioate, S-methyl 1,2,3-benzothiadiazole-7-carbothioate, spiro[2H]-1-benzopyrane-2,1'(3'H)-isobenzofuran]-3'-one, 4-[(3,4-dimethoxyphenyl)-3-(4-fluorophenyl)-acryloyl]-morpholine.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,

*Bacillus popilliae, Bacillus sphaericus, Bacillus subtilis, Bacillus thuringiensis,* baculoviruses, *Beauveria bassiana, Beauveria tenella,* bendiocarb, benfuracarb, bensultap, benzoximate, betacyfluthrin, bifenazate, bifenthrin, bioethanomethrin, biopermethrin, bistrifluron, BPMC, bromophos A, bufencarb, buprofezin, butathiofos, butocarboxim, butylpyridaben, cadusafos, carbaryl, carbofuran, carbophenothion, carbosulphan, cartap, chloethocarb, chlorethoxyfos, chlorfenapyr, chlorfenvinphos, chlorfluazuron, chlormephos, chlorpyrifos, chlorpyrifos M, chlovaporthrin, chromafenozide, cis-resmethrin, cispermethrin, clocythrin, cloethocarb, clofentezine, clothianidine, cyanophos, cycloprene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, dicofol, diflubenzuron, dimethoate, dimethylvinphos, diofenolan, disulphoton, docusat-sodium, dofenapyn, eflusilanate, emamectin, empenthrin, endosulphan, *Entomopfthora* spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazuron, flubrocythrinate, flucycloxuron, flucythrinate, flufenoxuron, flumethrin, flutenzine, fluvalinate, fonophos, fosmethilan, fosthiazate, ftubfenprox, furathiocarb, granulosis viruses, halofenozide, HCH, heptenophos, hexaflumuron, hexythiazox, hydroprene, imidacloprid, indoxacarb, isazofos, isofenphos, isoxathion, ivermectin, nuclear polyhedrosis viruses, lambda-cyhalothrin, lufenuron, malathion, mecarbam, metaldehyde, methamidophos, *Metharhizium anisopliae, Metharhizium flavoviride,* methidathion, methiocarb, methoprene, methomyl, methoxyfenozide, metolcarb, metoxadiazone, mevinphos, milbemectin, milbemycin, monocrotophos, naled, nitenpyram, nithiazine, novaluron, omethoate, oxamyl, oxydemethon M,

*Paecilomyces fumosoroseus,* parathion A, parathion M, permethrin, phenthoate, phorat, phosalone, phosmet, phosphamidon, phoxim, pirimicarb, pirimiphos A, pirimiphos M, profenofos, promecarb, propargite, propoxur, prothiofos, prothoat, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, spirodiclofen, sulphotep, sulprofos, tau-fluvalinate, tebufenozide, tebufenpyrad, tebupirimiphos, teflubenzuron, tefluthrin, temephos, temivinphos, terbufos, tetrachlorvinphos, tetradifon theta-cypermethrin, thiacloprid, thiamethoxarn, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii,*

YI 5302, Zeta-cypermethrin, Zolaprofos (1R-cis)-[5-(phenylmethyl)-3-franyl]-methyl-3-[(dihydro-2-oxo-3(2H)-furanylidene)-methyl]-2,2-dimethylcyclopropanecarboxylate, (3-phenoxyphenyl)-methyl-2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl)phenyl]-4,5-dihydro-oxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate 4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone,

*Bacillus thuringiensis* strain EG-2348,

[2-benzoyl-1-(1,1-dimethylethyl)-hydrazinobenzoic acid, 2,2-dimethyl-3-(2,4-dichlorophenyl)-2-oxo-1-oxaspiro[4.5]dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl[2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N"-nitro-guanidine, N-methyl-N'-(1-methyl-2-propenyl)-1,2-hydrazinedicarbothioamide, N-methyl-N'-2-propenyl-1,2-hydrazinedicarbothioamide, O,O-diethyl[2-(dipropylamino)-2-oxoethyl]-ethylphosphoramidothioate, N-cyanomethyl-4-trifluoromethyl-nicotinamide, 3,5-dichloro-1-(3,3-dichloro-2-propenyloxy)-4-[3-(5-trifluoromethylpyridine-2-yloxy)-propoxy]-benzene.

A mixture with other known active compounds, such as herbicides, or with fertilizers and growth regulators, is also possible.

In addition, the compounds of the formula (I) according to the invention also have very good antimycotic activity. They have a very broad antimycotic activity spectrum in particular against dermatophytes and yeasts, moulds and diphasic fungi, (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes, Microsporon* species such as *Microsporon canis* and *audouinii*. The list of these fungi by no means limits the mycotic spectrum covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10,000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10,000 g/ha, preferably between 1 and 5000 g/ha.

As already mentioned above, it is possible to treat all plants and their parts with active compounds according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetical engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, varieties, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defence of the plants against insects by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasized are the increased defence of the plants to fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucoton® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylurea, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plants will be developed and/or marketed in the future.

The plants listed can be treated according to the invention in a particularly advantageous manner with the compounds of the formula (I) according to the invention or the active compound mixtures according to the invention. The preferred ranges stated above for the active compounds or mixtures also apply to the treatment of these plants. Particular emphasis is given to the treatment of plants with the compounds and mixtures specifically mentioned in the present text.

The preparation and the use of the active compounds according to the invention is illustrated by the examples below.

PREPARATION EXAMPLES

Example 1

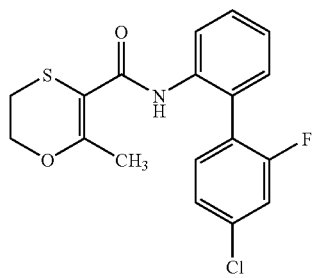

332 mg of 4'-chloro-2'-fluoro-1,1'-biphenyl-2-amine and 268 mg of 2-methyl-5,6-dihydro-1,4-oxathiine-3-carbonyl chloride are added dropwise to a suspension of 207 mg of potassium carbonate in 25 ml of acetonitrile. The reaction mixture is stirred for 10 h. For work-up, 20 ml of water are added to the reaction solution and the mixture is extracted with ethyl acetate. The organic phases are dried with sodium sulphate and concentrated. The residue is chromatographed on silica gel (cyclohexane/ethyl acetate 2:1).

This gives 220 mg (39%) of N-(4'-chloro-2'-fluoro-1,1'-biphenyl-2-yl)-2-methyl-5,6-dihydro-1,4-oxathiine-3-carboxamide of logP (pH 2.3)=3.61.

The oxathiinecarboxamides of the formula (I) listed in Table 1 below are likewise prepared analogously to Example 1 described above and in accordance with the general descriptions of the processes.

TABLE 1

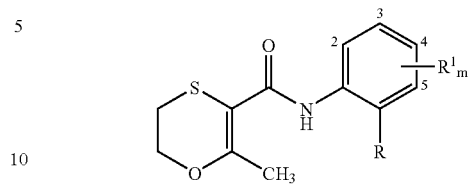

(I)

| Ex. | M | $R^1$ | R | logP (pH 2.3)/m.p. |
|---|---|---|---|---|
| 2 | 0 | — |  (4-CF$_3$-phenyl) | 3.97 |
| 3 | 0 | — | 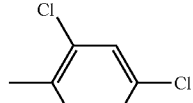 (4-OCF$_3$-phenyl) | 4.21 |
| 4 | 0 | — | (4-SCH$_3$-phenyl) | 3.83 |
| 5 | 0 | — | (4-Br-phenyl) | 3.89 |
| 6 | 0 | — | 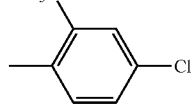 (2,3-diCl) | 4.02 / 97° C. |
| 7 | 0 | — | 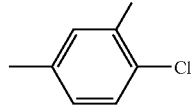 (2,4-diCl) | — |
| 8 | 0 | — | 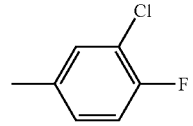 (2-CH$_3$, 4-Cl) | 4.26 |
| 9 | 0 | — | 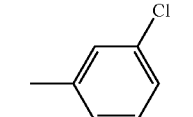 (2-F, 4-Cl) | 3.67 |
| 10 | 0 | — | 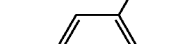 (2-Cl, 4-F) | 3.70 |
| 11 | 0 | — | (3,5-diCl) | 4.22 |
| 12 | 0 | — | 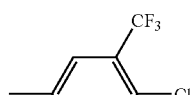 (2,3-diF) | 3.38 |
| 13 | 0 | — | 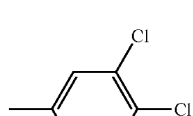 (2-CF$_3$, 4-Cl) | 4.03 |
| 14 | 1 | 4-F | (2,3-diCl) | 4.00 |

TABLE 1-continued (I)

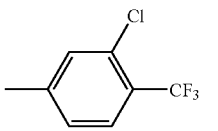

| Ex. | M | R¹ | R | logP (pH 2.3)/m.p. |
|---|---|---|---|---|
| 15 | 0 | — | 4-CH₃, 2-Cl phenyl | 4.17 |
| 16 | 1 | 2-F | 4-Cl, 5-Cl phenyl | 3.53 |
| 17 | 0 | — | 4-Cl phenyl | 3.69 |
| 18 | 0 | — | 2-F, 4-F phenyl | 3.24 |
| 19 | 0 | — | 4-CN phenyl | 2.74 |
| 20 | 0 | — | 2-F, 4-CF₃ phenyl | 3.76  117–119° C. |
| 21 | 0 | — | 4-CH₃, 5-F phenyl | 3.80 |
| 22 | 0 | — | 2-Cl, 4-CH₃ phenyl | — |
| 23 | 0 | — | 2-F, 4-CH₃ phenyl | 3.56 |
| 24 | 0 | — | 3-F, 5-F phenyl | 3.38 oil |
| 25 | 0 | — | 2-Cl, 4-CF₃ phenyl | 4.02  103–105° C. |

The logP values given in the Preparation Examples were determined in accordance with EEC Directive 79/831 Annex V.A8 by HPLC (High Performance Liquid Chromatography) using a reversed-phase column (C 18). Temperature: 43° C.

Mobile phases for the determination in the acidic range: 0.1% aqueous phosphoric acid, acetonitrile; linear gradients from 10% acetonitrile to 90% acetonitrile.

Calibration was carried out using unbranched alkan-2-ones (having 3 to 16 carbon atoms) with known logP values (determination of the logP values by the retention times using linear interpolation between two successive alkanones).

The lambda max values were determined in the maxima of the chromatographic signals using the UV spectra from 200 m to 400 nm.

USE EXAMPLES

Example A

*Podosphaera* Test (Apple)/Protective

Solvents: 24.5 Parts by weight of acetone 24.5 Parts by weight of dimethylacetamide Emulsifier: 1.0 Part by weight of alkylaryl polyglycol ether To produce a suitable preparation of active compound, 1 part by weight of active compound is mixed with the stated amount of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of the apple mildew pathogen *Podosphaera leucotricha*. The plants are then placed in a greenhouse at about 23° C. and a relative atmospheric humidity of about 70%.

Evaluation is carried out 10 days after the inoculation. 0% means an efficacy which corresponds to that of the control, whereas an efficacy of 100% means that no infection is observed.

Active compounds, application rates and test results are shown in the table below.

TABLE A

Podosphaera Test (Apple)/protective

| Active compound | | Active compound application rate in g/ha | Efficacy in % |
|---|---|---|---|
| 6 | [structure: 2-methyl-1,4-oxathiine-3-carboxamide with 3,4-dichlorobiphenyl] | 100 | 100 |
| 9 | [structure: 2-methyl-1,4-oxathiine-3-carboxamide with 4-chloro-3-fluorobiphenyl] | 100 | 100 |
| 10 | [structure: 2-methyl-1,4-oxathiine-3-carboxamide with 3-chloro-4-fluorobiphenyl] | 100 | 93 |
| 15 | [structure: 2-methyl-1,4-oxathiine-3-carboxamide with 4-chloro-3-methylbiphenyl] | 100 | 98 |
| 16 | [structure: 2-methyl-1,4-oxathiine-3-carboxamide with 2-fluoro-3',4'-dichlorobiphenyl] | 100 | 90 |
| 7 | [structure: 2-methyl-1,4-oxathiine-3-carboxamide with 2,4-dichlorobiphenyl] | 100 | 100 |
| 8 | [structure: 2-methyl-1,4-oxathiine-3-carboxamide with 4-chloro-2-methylbiphenyl] | 100 | 96 |
| 1 | [structure: 2-methyl-1,4-oxathiine-3-carboxamide with 4-chloro-2-fluorobiphenyl] | 100 | 99 |

Example B

| Venturia Test (Apple)/protective | |
|---|---|
| Solvents: | 24.5 Parts by weight of acetone |
| | 24.5 Parts by weight of dimethylacetamide |
| Emulsifier: | 1.0 Part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the apple scab pathogen *Venturia inaequalis* and then remain in an incubation cabin at about 20° C. and 100% relative atmospheric humidity for 1 day.

The plants are then placed in a greenhouse at about 21° C. and a relative atmospheric humidity of about 90%.

Evaluation is carried out 10 days after the inoculation. 0% means an efficacy which corresponds to that of the control, whereas an efficacy of 100% means that no infection is observed.

Active compounds, application rates and test results are shown in the table below.

TABLE B

*Venturia* Test (Apple)/protective

| Active compound | Active compound in g/ha | Efficacy in % |
|---|---|---|
| 6 | 100 | 100 |
| 9 | 100 | 100 |
| 10 | 100 | 100 |
| 15 | 100 | 100 |

TABLE B-continued

*Venturia* Test (Apple)/protective

| Active compound | Active compound in g/ha | Efficacy in % |
|---|---|---|
| 16 | 100 | 100 |
| 17 | 100 | 93 |
| 7 | 100 | 100 |
| 8 | 100 | 99 |
| 12 | 100 | 100 |

TABLE B-continued

*Venturia* Test (Apple)/protective

| Active compound | Active compound in g/ha | Efficacy in % |
|---|---|---|
| 13 (structure: dihydrooxathiine-carboxamide linked to 2-(4-chloro-3-trifluoromethylphenyl)phenyl) | 100 | 99 |
| 1 (structure: dihydrooxathiine-carboxamide linked to 2-(4-chloro-2-fluorophenyl)phenyl) | 100 | 100 |

Example C

| Alternaria Test (Tomato)/protective | |
|---|---|
| Solvent: | 49 Parts by weight of N,N-dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young tomato plants are sprayed with the preparation of active compound at the stated application rate. 1 day after the treatment, the plants are inoculated with an aqueous spore suspension of *Alternaria solani*. The plants are then placed in an incubation cabin at about 20° C. and 100% relative atmospheric humidity.

Evaluation is carried out 2 days after the inoculation. 0% means an efficacy which corresponds to that of the control, whereas an efficacy of 100% means that no infection is observed.

Active compounds, application rates and test results are shown in the table below.

TABLE C

*Alternaria* Test (Tomato)/protective

| Active compound | Active compound in g/ha | Efficacy in % |
|---|---|---|
| 6 (structure: dihydrooxathiine-carboxamide linked to 2-(3,4-dichlorophenyl)phenyl) | 100 | 100 |
| 9 (structure: dihydrooxathiine-carboxamide linked to 2-(4-chloro-3-fluorophenyl)phenyl) | 100 | 100 |
| 10 (structure: dihydrooxathiine-carboxamide linked to 2-(3-chloro-4-fluorophenyl)phenyl) | 100 | 94 |
| 15 (structure: dihydrooxathiine-carboxamide linked to 2-(4-chloro-3-methylphenyl)phenyl) | 100 | 96 |
| 16 (structure: dihydrooxathiine-carboxamide linked to 2-fluoro-6-(3,4-dichlorophenyl)phenyl) | 100 | 95 |

TABLE C-continued

Alternaria Test (Tomato)/protective

| Active compound | | Active compound in g/ha | Efficacy in % |
|---|---|---|---|
| 17 | 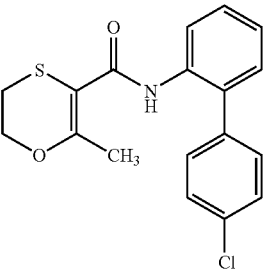 | 100 | 93 |
| 7 | 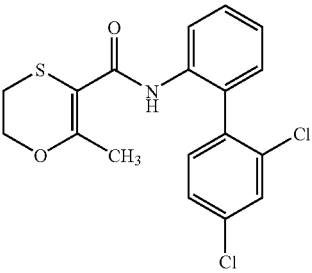 | 100 | 98 |
| 8 | 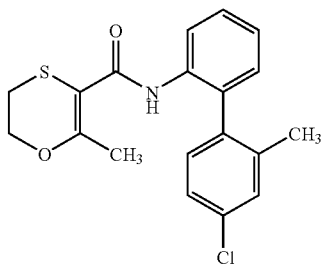 | 100 | 94 |
| 12 | 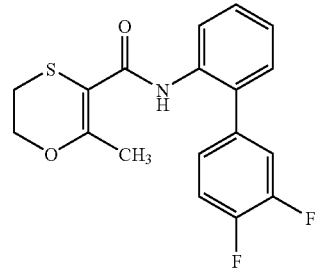 | 100 | 95 |
| 13 | 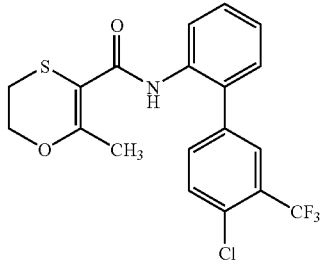 | 100 | 94 |
| 1 | 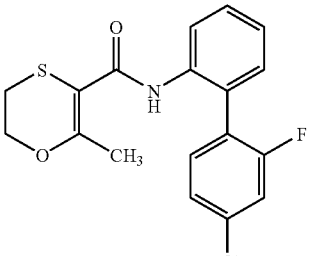 | 100 | 94 |

Example D

| Pyrenophora teres Test (Barley)/protective | |
|---|---|
| Solvent: | 25 Parts by weight of N,N-dimethylacetamide |
| Emulsifier: | 0.6 Part by weight of alkylaryl polyglycol ether |

To produce a suitable preparation of active compound, 1 part by weight of active compound is mixed with the stated amount of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Pyrenophora teres*. The plants remain in an incubation cabin at 20° C. and 100% relative atmospheric humidity for 48 hours.

The plants are then placed in a greenhouse at temperature of about 20° C. and a relative atmospheric humidity of about 80%.

Evaluation is carried out 7 days after the inoculation. 0% means an efficacy which corresponds to that of the control, whereas an efficacy of 100% means that no infection is observed.

Active compounds, application rates and test results are shown in the table below.

TABLE D

Pyrenophora teres - Test (Barley)/protective

| Active compound | | Active compound in g/ha | Efficacy in % |
|---|---|---|---|
| 9 | 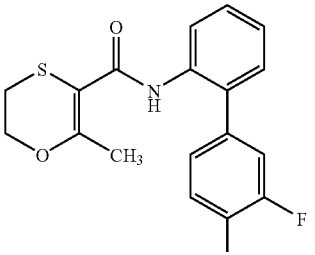 | 500 | 95 |

37

TABLE D-continued

Pyrenophora teres - Test (Barley)/protective

| Active compound | Active compound in g/ha | Efficacy in % |
|---|---|---|
| 17 | 500 | 100 |
| 19 | 500 | 93 |

Example E

| Puccinia Test (Wheat)/protective | |
|---|---|
| Solvent: | 25 parts by weight of N,N-dimethylacetamide |
| Emulsifier: | 0.6 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Puccinia recondita*. The plants remain in an incubation cabin at 20° C. and 100% relative atmospheric humidity for 48 hours.

The plants are then placed in a greenhouse at a temperature of about 20° C. and a relative atmospheric humidity of about 80% to promote the development of rust pustules.

Evaluation is carried out 10 days after the inoculation. 0% means an efficacy which corresponds to that of the control, whereas an efficacy of 100% means that no infection is observed.

Active compounds, application rates and test results are shown in the table below.

38

TABLE E

Puccinia Test (Wheat)/protective

| Active compound | Active compound in g/ha | Efficacy in % |
|---|---|---|
| 9 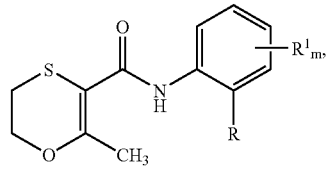 | 500 | 100 |
| 6 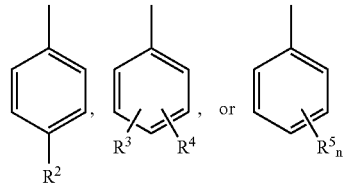 | 500 | 100 |

What is claimed is:

1. An oxathiinecarboxamide of formula (I)

(I)

in which

R$^1$ represents fluorine, m represents 0, 1, or 2,

R represents one of the groups

R$^2$ represents chlorine, bromine, iodine, cyano, nitro, C$_1$–C$_8$-alkyl, C$_1$–C$_8$-alkoxy, C$_1$–C$_8$-alkylthio, C$_1$–C$_6$-haloalkyl, C$_1$–C$_6$-haloalkoxy, or C$_1$–C$_6$-haloalkylthio, each halo-containing group having from 1 to 13 fluorine, chlorine, and/or bromine atoms, R$^3$ and R$^4$ independently of one another represent fluorine, chlorine, bromine, iodine, cyano, nitro, C$_1$–C$_8$-alkyl, C$_1$–C$_8$-alkoxy, C$_1$–C$_8$-alkylthio, C$_1$–C$_6$-haloalkyl, C$_1$–C$_6$-haloalkoxy, or C$_1$–C$_6$-haloalkylthio, each halo-containing group having 1 to 13 fluorine, chlorine, and/or bromine atoms, n represents 3, 4, or 5, and R⁵ represents identical or different radicals selected from the group consisting of fluorine, chlorine, bromine, iodine, cyano, nitro, $C_1$–$C_8$-alkyl, $C_1$–$C_8$-alkoxy, $C_1$–$C_8$-alkylthio, $C_1$–$C_6$-haloalkyl, $C_1$–$C_6$-haloalkoxy, and $C_1$–$C_6$-haloalkylthio, each halo-containing group having 1 to 13 fluorine, chlorine, and/or bromine atoms.

2. An oxathiinecarboxamide of formula (I) according to claim 1 in which

R¹ represents fluorine, m represents 0, 1, or 2,

R represents one of the groups

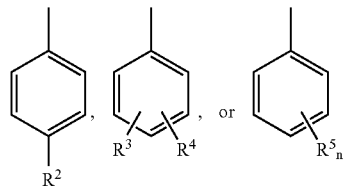

R² represents chlorine, bromine, cyano, $C_1$–$C_6$-alkyl, $C_1$–$C_6$-alkoxy, $C_1$–$C_6$-alkylthio, $C_1$–$C_4$-haloalkyl, $C_1$–$C_4$-haloalkoxy, or $C_1$–$C_4$-haloalkylthio, each halo-containing group having 1 to 9 fluorine, chlorine, and/or bromine atoms, R³ and R⁴ independently of one another represent fluorine, chlorine, bromine, $C_1$–$C_6$-alkyl, $C_1$–$C_6$-alkoxy, $C_1$–$C_6$-alkylthio, $C_1$–$C_4$-haloalkyl, $C_1$–$C_4$-haloalkoxy, or $C_1$–$C_4$-haloalkylthio, each halo-containing group having 1 to 9 fluorine, chlorine, and/or bromine atoms, n represents 3, 4, or 5, and R⁵ represents identical or different radicals selected from the group consisting of fluorine, chlorine, bromine, $C_1$–$C_6$-alkyl, $C_1$–$C_6$-alkoxy, $C_1$–$C_6$-alkylthio, $C_1$–$C_4$-haloalkyl, $C_1$–$C_4$-haloalkoxy, and $C_1$–$C_4$-haloalkylthio, each halo-containing group having 1 to 9 fluorine, chlorine, and/or bromine atoms.

3. An oxathiinecarboxamide of formula (I) according to claim 1 in which

R¹ represents fluorine, m represents 0 or 1,

R represents one of the groups

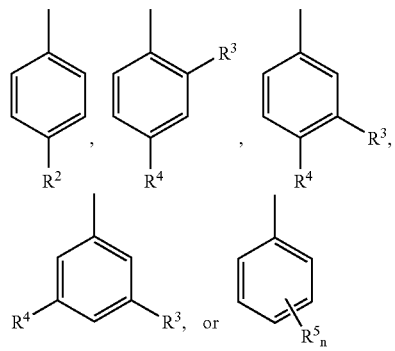

R² represents chlorine, bromine, cyano, methyl, ethyl, n-propyl, i-propyl, n-butyl, i-butyl, s-butyl, t-butyl, methoxy, ethoxy, methylthio, ethylthio, trichloromethyl, trifluoromethyl, difluoromethyl, difluorochloromethyl, difluoromethoxy, trifluoromethoxy, trifluoromethylthio, or difluorochloromethylthio, R³ and R⁴ independently of one another represent fluorine, chlorine, bromine, methyl, ethyl, n-propyl, i-propyl, n-butyl, i-butyl, s-butyl, t-butyl, methoxy, ethoxy, methylthio, ethylthio, trichloromethyl, trifluoromethyl, difluoromethyl, difluorochloromethyl, difluoromethoxy, trifluoromethoxy, trifluoromethylthio, or difluorochloromethylthio, n represents 3 or 4, and R⁵ represents identical or different radicals selected from the group consisting of fluorine, chlorine, bromine, methyl, ethyl, n-propyl, i-propyl, n-butyl, i-butyl, s-butyl, t-butyl, methoxy, ethoxy, methylthio, ethylthio, trichloromethyl, trifluoromethyl, difluoromethyl, difluorochloromethyl, difluoromethoxy, trifluoromethoxy, trifluoromethylthio, and difluorochloromethylthio.

4. An oxathiinecarboxamide of formula (I) according to claim 1 in which

R¹ represents fluorine, m represents 0 or 1,

R represents one of the groups

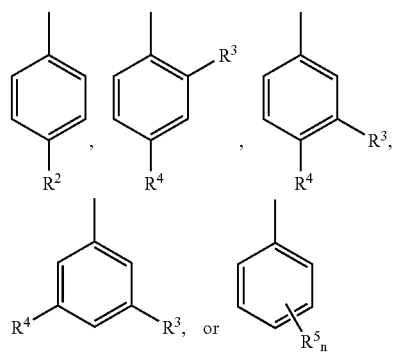

R² represents chlorine, bromine, cyano, methyl, ethyl, n-propyl, i-propyl, n-butyl, i-butyl, s-butyl, t-butyl, methoxy, ethoxy, methylthio, ethylthio, trichloromethyl, trifluoromethyl, difluoromethyl, trifluoromethoxy, or trifluoromethylthio, R³ and R⁴ independently of one another represent fluorine, chlorine, bromine, methyl, ethyl, n-propyl, i-propyl, n-butyl, i-butyl, s-butyl, t-butyl, methoxy, ethoxy, methylthio, ethylthio, trichloromethyl, trifluoromethyl, difluoromethyl, trifluoromethoxy, or trifluoromethylthio, n represents 3, and R⁵ represents identical or different radicals selected from the group consisting of fluorine, chlorine, bromine, methyl, ethyl, n-propyl, i-propyl, n-butyl, i-butyl, s-butyl, t-butyl, methoxy, ethoxy, methylthio, ethylthio, trichloromethyl, trifluoromethyl, difluoromethyl, trifluoromethoxy, and trifluoromethylthio.

5. An oxathiinecarboxamide of formula (I) according to claim 1 in which $R^1$ represents fluorine, m represents 0 or 1, represents one of the groups

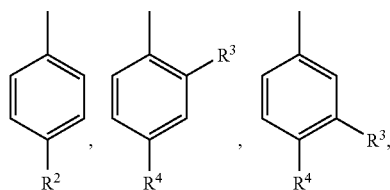

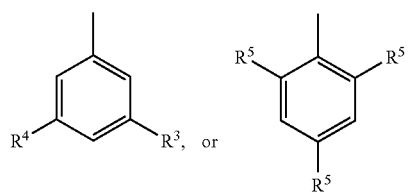

$R^2$ represents chlorine, bromine, cyano, t-butyl, methoxy, methylthio, trichloromethyl, trifluoromethyl, trifluoromethoxy, or trifluoromethylthio, $R^3$ and $R^4$ independently of one another represent fluorine, chlorine, methyl, methoxy, methylthio, trifluoromethyl, trifluoromethoxy, or trifluoromethylthio, and $R^5$ represents identical or different radicals selected from the group consisting of fluorine, chlorine, methyl, methoxy, methylthio, trifluoromethyl, trifluoromethoxy, and trifluoromethylthio.

6. An oxathiinecarboxamide according to claim 1 of formula (I-a)

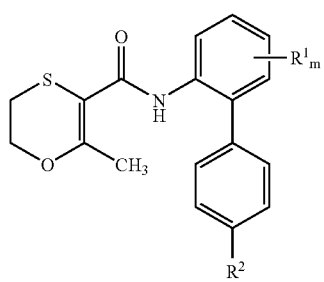

(I-a)

in which $R^1$ represents fluorine, m represents 0 or 1, and $R^2$ represents chlorine, bromine, cyano, methyl, ethyl, n-propyl, i-propyl, n-butyl, i-butyl, s-butyl, t-butyl, methoxy, ethoxy, methylthio, ethylthio, trichloromethyl, trifluoromethyl, difluoromethyl, difluorochloromethyl, difluoromethoxy, trifluoromethoxy, trifluoromethylthio, or difluorochloromethylthio.

7. An oxathiinecarboxamide according to claim 1 of formula (I-b)

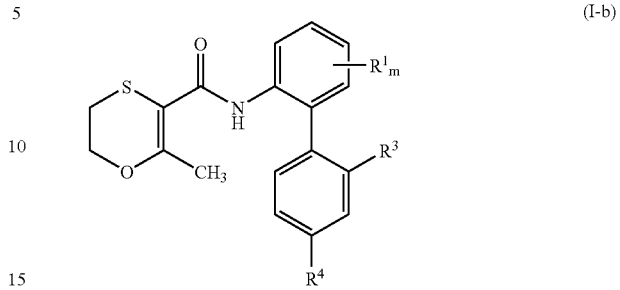

(I-b)

in which $R^1$ represents fluorine, m represents 0 or 1, and $R^3$ and $R^4$ independently of one another represent fluorine, chlorine, bromine, methyl, ethyl, n-propyl, i-propyl, n-butyl, i-butyl, s-butyl, t-butyl, methoxy, ethoxy, methylthio, ethylthio, trichloromethyl, trifluoromethyl, difluoromethyl, difluorochloromethyl, difluoromethoxy, trifluoromethoxy, trifluoromethylthio, or difluorochloromethylthio.

8. An oxathiinecarboxamide according to claim 1 of formula (I-c)

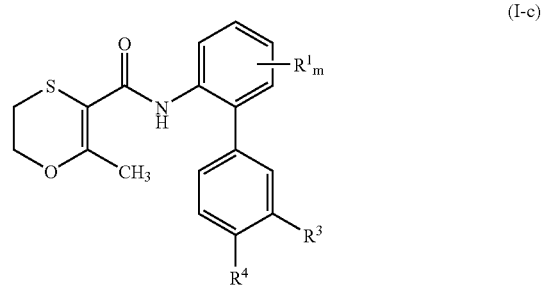

(I-c)

in which $R^1$ represents fluorine, m represents 0 or 1, and $R^3$ and $R^4$ independently of one another represent fluorine, chlorine, bromine, methyl, ethyl, n-propyl, i-propyl, n-butyl, i-butyl, s-butyl, t-butyl, methoxy, ethoxy, methylthio, ethylthio, trichloromethyl, trifluoromethyl, difluoromethyl, difluorochloromethyl, difluoromethoxy, trifluoromethoxy, trifluoromethylthio, or difluorochloromethylthio.

9. An oxathiinecarboxamide according to claim 1 of formula (I-d)

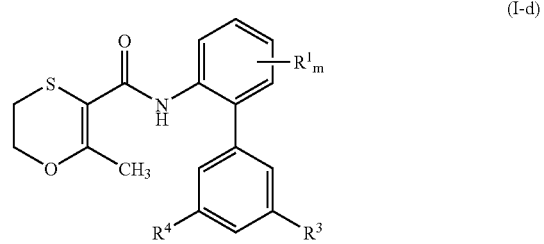

(I-d)

in which $R^1$ represents fluorine, m represents 0 or 1, and $R^3$ and $R^4$ independently of one another represent fluorine, chlorine, bromine, methyl, ethyl, n-propyl, i-propyl, n-butyl, i-butyl, s-butyl, t-butyl, methoxy, ethoxy, methylthio, ethylthio, trichloromethyl, trifluoromethyl, difluoromethyl, difluorochloromethyl, difluoromethoxy, trifluoromethoxy, trifluoromethylthio, or difluorochloromethylthio.

10. A process for preparing oxathiinecarboxamides of formula (I) according to claim 1 comprising (a) reacting a carboxylic acid derivative of formula (II)

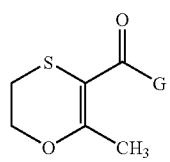

(II)

in which G represents halogen, hydroxyl, or $C_1$–$C_6$-alkoxy, with an aniline derivative of formula (III)

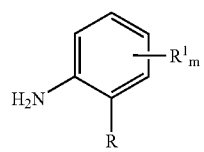

(III)

in which R, $R^1$, and m are as defined for formula (I) in claim 1, optionally in the presence of a catalyst, optionally in the presence of an acid binder, and optionally in the presence of a diluent, or (b) reacting a carboxamide derivative of formula (IV)

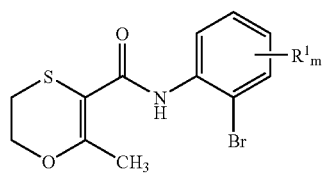

(IV)

in which $R^1$ and m are as defined for formula (I) in claim 1, with a boronic acid derivative of formula (V)

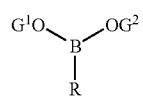

(V)

in which

R is as defined for formula (I) in claim 1, and $G^1$ and $G^2$ each represent hydrogen or together represent tetramethylethylene, in the presence of a catalyst, optionally in the presence of an acid binder, and optionally in the presence of a diluent, or (c) reacting a carboxamide boronic acid derivative of formula (VI)

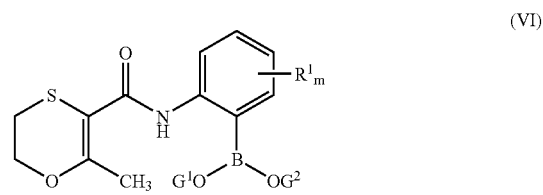

(VI)

in which $R^1$ and m are as defined for formula (I) in claim 1, and $G^1$ and $G^2$ each represent hydrogen or together represent tetramethylethylene, with a phenyl derivative of formula (VII)

(VII)

in which R is as defined for formula (I) in claim 1, in the presence of a catalyst, optionally in the presence of an acid binder, and optionally in the presence of a diluent, or (d) reacting a carboxamide derivative of formula (IV)

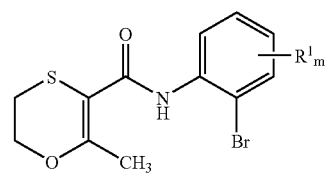

(IV)

in which $R^1$ and m are as defined for formula (I) in claim 1, with a phenyl derivative of formula (VII)

(VII)

in which R is as defined for formula (I) in claim 1, in the presence of a palladium or platinum catalyst, in the presence of 4,4,4',4',5,5,5',5'-octamethyl-2,2'-bis-1,3,2-dioxaborolane, optionally in the presence of an acid binder, and optionally in the presence of a diluent.

11. A composition for controlling unwanted micro-organisms comprising one or more oxathiinecarboxamides of formula (I) according to claim 1 and one or more extenders and/or surfactants.

12. A method for controlling unwanted micro-organisms comprising applying an effective amount of one or more oxathiinecarboxamide of formula (I) according to claim 1 to the micro-organisms and/or their habitat.

13. A process for preparing compositions for controlling unwanted micro-organisms comprising mixing one or more oxathiinecarboxamides of formula (I) according to claim 1 with one or more extenders and/or surfactants.

* * * * *